United States Patent [19]

Herbert

[11] 4,429,956

[45] * Feb. 7, 1984

[54] WET CORNEA TELESCOPE

[76] Inventor: M. Linton Herbert, 762 E. Michigan Ave., Orlando, Fla. 32806

[ * ] Notice: The portion of the term of this patent subsequent to Jun. 15, 1999 has been disclaimed.

[21] Appl. No.: 369,898

[22] Filed: Apr. 19, 1982

Related U.S. Application Data

[63] Continuation of Ser. No. 113,498, Jan. 21, 1980, abandoned.

[51] Int. Cl.[3] ........................ G02B 3/12; G02B 17/00; G02B 21/04; G02B 23/02

[52] U.S. Cl. .................................... 350/410; 350/418; 350/444; 350/507; 350/537; 351/160 R; 351/160 H

[58] Field of Search ............... 350/410, 418, 442, 507, 350/444, 537; 351/160 R, 160 H

[56] References Cited

U.S. PATENT DOCUMENTS 4,334,736 6/1982 Herbert ............................... 350/418

OTHER PUBLICATIONS

Drysdale, C. V.; "Small Telescopes and Binoculars"; *The Proceedings of the Optical Convention;* Norgate & Williams; London; 1905; p. 127.

*Primary Examiner*—John K. Corbin
*Assistant Examiner*—Scott J. Sugarman
*Attorney, Agent, or Firm*—Cahill, Sutton & Thomas

[57] ABSTRACT

A wet cornea telescope permits a viewer to see a magnified image of a remotely positioned object. The telescope includes a fluid-filled eyepiece which is positioned in contact with the cornea of one of the viewer's eyes. The eyepiece includes an optically transparent window and forms an optically transparent, fluid-filled chamber between the cornea of the viewer's eye and the window. A light converging device is interposed in the optical path between the object and the eyepiece to converge light rays travelling from the object to the viewer's eye to thereby project a magnified image on the viewer's retina.

40 Claims, 14 Drawing Figures

22
10
20
14
18
16
24

24

34

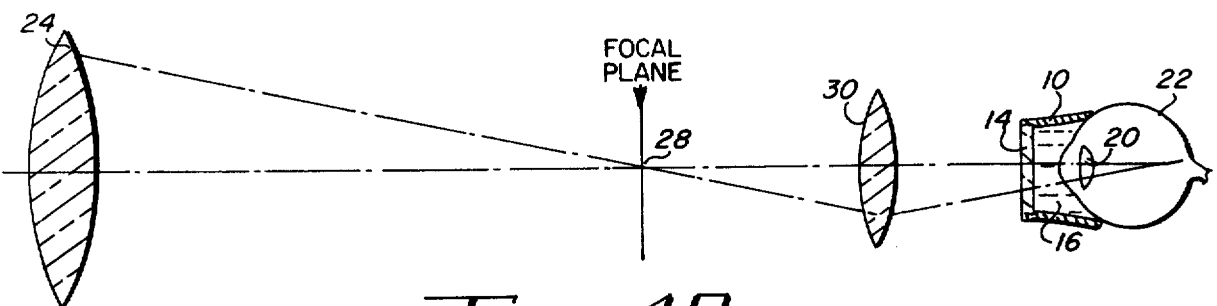
FIG. 10
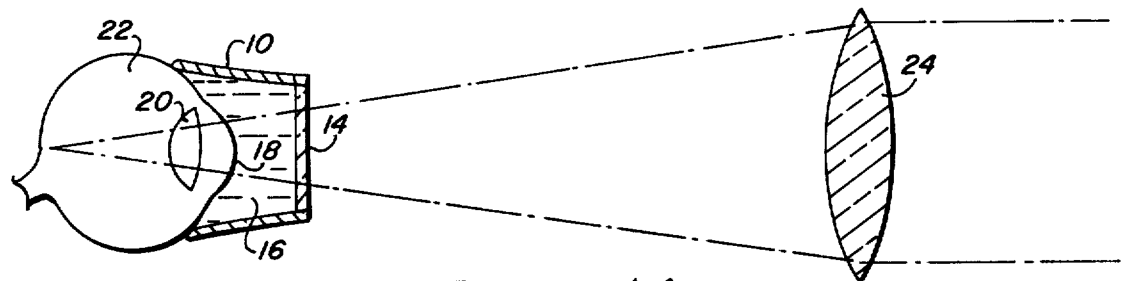
FIG. 11
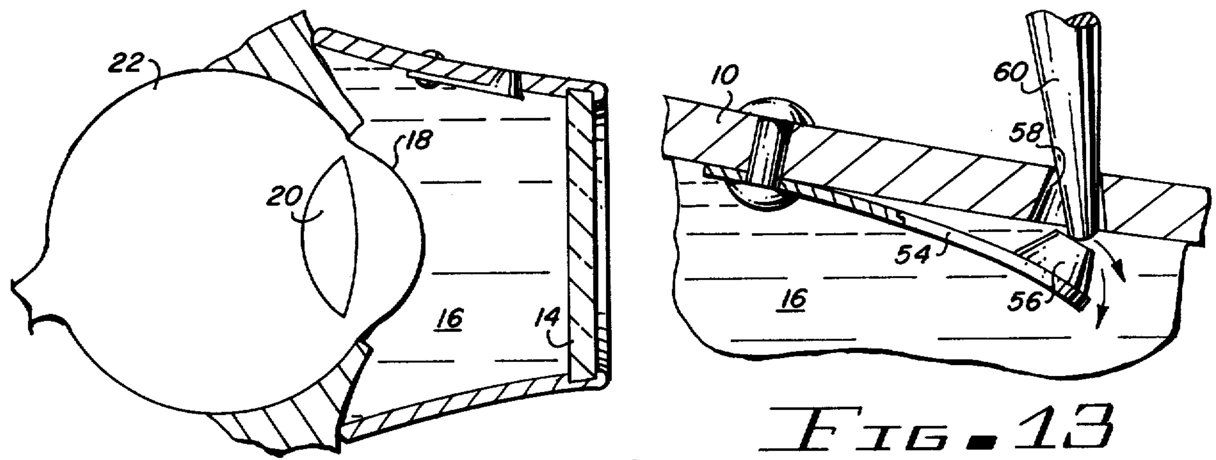
FIG. 12
FIG. 13
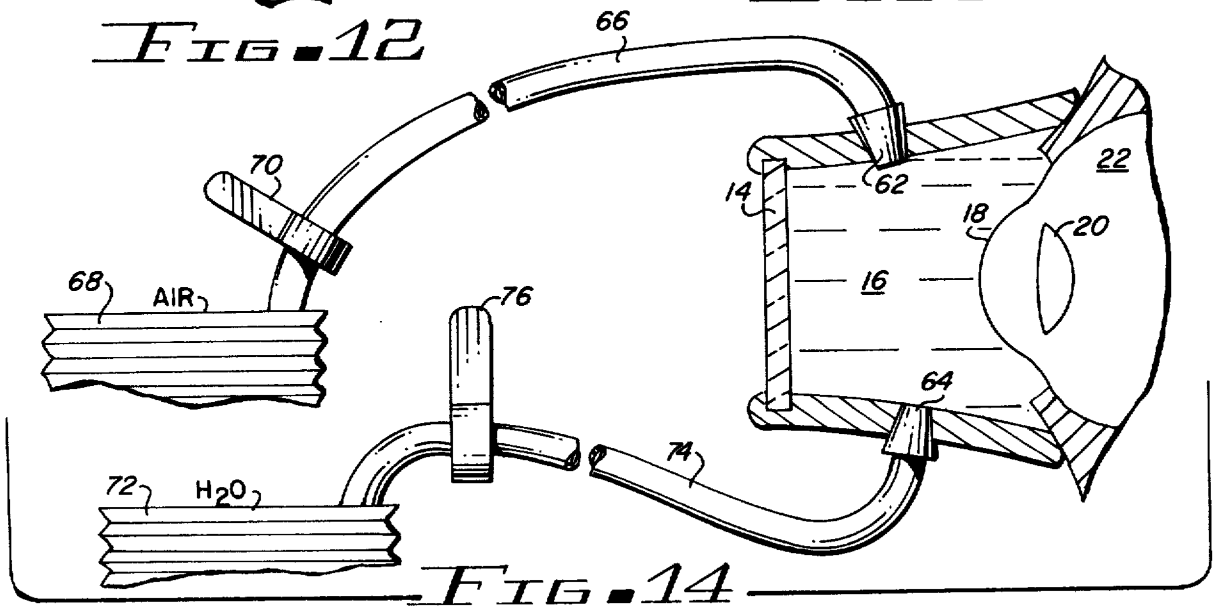
FIG. 14

WET CORNEA TELESCOPE

This is a continuation of application, Ser. No. 113,498, filed Jan. 21, 1980 now abandoned.

BACKGROUND OF THE INVENTION

1. Field of the Invention

The present invention relates to telescopes, and more particularly, to telescopes including an eyepiece which forms a fluid-filled chamber about the cornea of the viewer's eye.

2. Description of the Prior Art.

The prior art discloses numerous different types of telescopes of various different designs which are generally well known to those skilled in the art. Low magnification telescopes can be made inexpensively, but as the magnification power achieved by telescope increases substantially, the purchase cost of the telescope increases rapidly.

U.S. Pat. No. 3,010,109 (Gray) discloses fluid-filled goggles which cause the cornea of the wearer's eye to be immersed in a fluid such as distilled water. A positive refractive lens is positioned on the front surface of each goggle eyepiece to compensate for the refractive changes caused by wearing this device to thereby permit the user to see as normally as possible. This device provides protection to the user's eye from the adverse affects of acceleration and deceleration forces. The fluid within each of the goggle eyepieces acts as a buffer to prevent displacement of the eyeballs during periods of high G stress by providing support for the eyeballs.

SUMMARY OF THE INVENTION

It is therefore a primary object of the present invention to provide an inexpensive, rugged high power telescope.

Another object of the present invention is to provide a wet cornea telescope which immerses the cornea of the viewer's eye in a fluid having an index of refraction comparable to the index of refraction of the transparent fluid contained within the viewer's eye to thereby eliminate refractive effects of the corneal surface of the viewer's eye.

Another object of the present invention is to provide a wet cornea telescope which substantially reduces chromatic aberration of the type generally produced by the corneal surface of the viewer's eye.

Another object of the present invention is to provide a wet cornea telescope which is compatible with various types of optical converging devices to form a high magnification telescope.

Briefly stated, and in accord with one embodiment of the invention, a wet cornea telescope permits a viewer to see a magnified image of a remotely positioned object. The telescope includes a fluid-filled eyepiece which is coupled to the face of the viewer in alignment with his eye. The eyepiece includes an optically transparent window for forming an optically transparent, fluid-filled chamber between the cornea of the viewer's eye and the window. Means is interposed in the optical path between the object and the eyepiece to converge light rays travelling from the object to the viewer's eye to thereby project a magnified image of the object on the viewer's retina.

DESCRIPTION OF THE DRAWINGS

The invention if pointed out with particularly in the appended claims. However, other objects and advantages together with the operation of the invention, may be better understood by reference to the following detailed description taken in connection with the following illustrations wherein:

FIG. 10 illustrates still another embodiment of the present invention including a second positive lens positioned between the first positive lens and the eyepiece of the present invention.

FIG. 11 is included to illustrate the method of calculating the magnification power of the present invention.

FIG. 12 illustrates an embodiment of the present invention having an eyepiece vent for introducing fluid into the eyepiece of the present invention.

FIG. 13 is an enlarged sectional view of the eyepiece illustrated in FIG. 12, particularly indicating the manner in which the eyepiece valve is opened.

FIG. 14 illustrates another embodiment of the eyepiece of the present invention which includes means for filling and draining fluid from the eyepiece without removing the eyepiece.

DESCRIPTION OF THE PREFERRED EMBODIMENT

In order to better illustrate the advantages of the invention and its contributions to the art, several preferred hardware embodiments of the invention will now be described in some detail.

Figure 1:
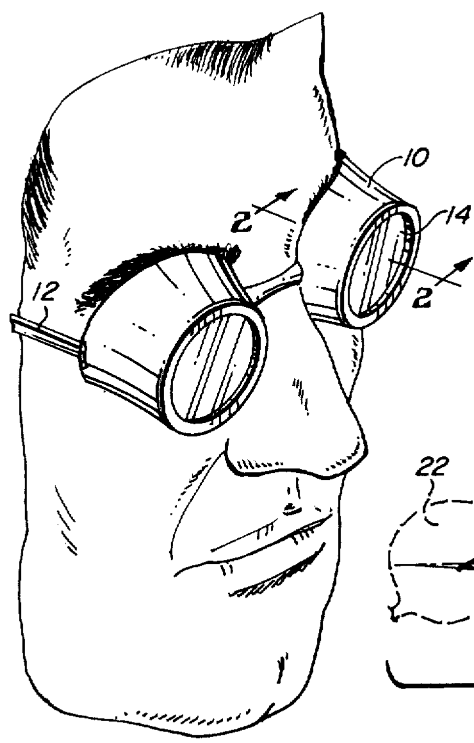
FIG. 1 is a partial perspective view illustrating a viewer wearing a pair of dual-eyepiece fluid-filled goggles.
Figure 2:
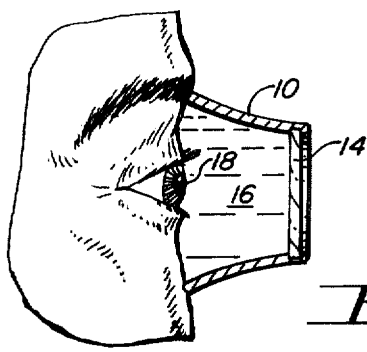
FIG. 2 is a side view of the goggles illustrated in FIG. 1, taken along section line 2—2, illustrating the fluid-filled chamber formed by the interface between the eyepiece of the present invention and the face of the viewer.
Figure 3:
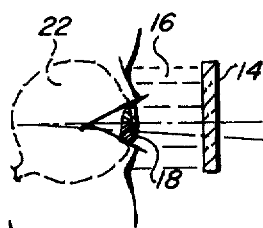
FIG. 3 illustrates the spatial arrangement of the various elements of the wet cornea telescope of the present invention.

Referring now to FIGS. 1, 2, 3 and 11, the first embodiment of the present invention will be described in some detail. Eyepiece 10 is maintained in a fixed position on the face of the viewer by strap 12 which passes around the viewer's head and includes first and second ends which are coupled to the left and right sides of eyepiece 10. As is illustrated in FIG. 1, a pair of swimmer's goggles including a pair of eyepieces can readily be adapted for use in connection with the present invention.

An optically transparent window 14 is coupled to the frontal section of eyepiece 10 and forms an optically transparent, fluid-filled chamber 16 between the cornea 18 of the viewer's eye and window 14. Cavity 16 can be filled with various different types of optically transparent fluids such as distilled or deionized water, a two and one half percent saline solution or a five percent sugar solution. The five percent sugar or sucrose solution performs best since it does not irritate the corneal surface as does the saline solution and in addition sugar provides nourishment to the corneal surface.

It is desirable to fill chamber 16 with a fluid which has an index of refraction as close as possible to the 1.333 index of refraction of the fluid within the aqueous humor of the viewer's eye. The index of refraction of the fluid within chamber 16 can be more or less than the desired 1.336 index of refraction, but the overall performance of the present invention is slightly reduced and chromatic aberration is introduced if the difference between the two refractive indices is substantial.

When a fluid having an index of refraction on the order of 1.336 is utilized to fill chamber 16, the refractive effect of the former air-cornea interface is virtually completely eliminated and the optical characterictics of the human eye are completely altered. In the embodiments being presently discussed in which window 14 is a flat, optically transparent surface, light waves which pass through window 14 and are projected onto the retina of the viewer's eye will not be refracted to any substantial degree by window 14 or cornea 18. In the system illustrated, light rays will be refracted only by lens 20 within eye 22.

The remaining element of the wet cornea telescope of the present invention comprises converging means such as a positive lens 24. Positive lens 24 is interposed in the optical path between the target or object to be examined and eyepiece 10. Lens 24 converges light rays travelling from the object to the viewer's eye as is illustrated by the dotted lines in FIGS. 3 and 11. In the telescope embodiment presently being discussed, lens 24 is a comparatively weak positive lens but can produce approximately a 40X magnification when separated from window 14 by a distance on the order of thirty inches. If desired, the viewer can maintain lens 24 in the desired position with one hand. In this embodiment the focal length of lens 24 must be greater than the spacing between eye 22 and lens 24.

In FIG. 11, dimension line A indicates the plane of the retina of eye 22; dimension line B represents the plane of lens 20; and dimension line C represents the plane of positive lens 24. The magnification power of the wet cornea telescope illustrated in FIG. 11 can be determined by computing the ratio of distance AC to distance AB. It is apparent then that the magnification of the telescope can be increased by increasing distance AC since distance AB remains constant.

Figure 4:
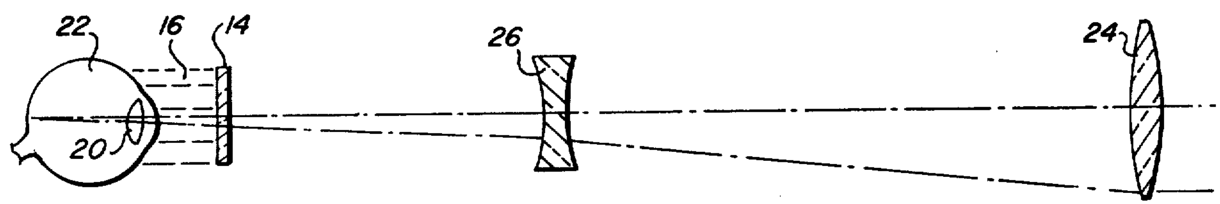
FIG. 4 illustrates an additional embodiment of the wet cornea telescope of the present invention which includes a negitive lens positioned between the eyepiece and the positive lens.

FIG. 4 illustrates one way in which distance AC can be further increased without changing the optical characteristics or focal length of lens 24. In this embodiment, lens 24 is positioned at a distance greater than its focal length in front of eye 22. A negative lens 26 is interposed in the light path between lens 24 and eye 22 as shown. This negative lens 26 causes the light rays refracted by lens 24 to diverge slightly which effectively lengthens the focal length of lens 24 as is illustrated by the dotted lines which are representatives of light rays.

FIG. 10 illustrates a second way in which distance AC can be increased. The focal plane of lens 24 is indicated by reference number 28. Lens 24 is positioned such that its focal plane 28 lies in front of window 14 of eye piece 10. A second positive lens 30 is then positioned between focal plane 28 and window 14 as illustrated at a position which causes light rays to strike lens 20 at an angle which permits lens 20 to focus the light rays to form an image on the retina of eye 22.

Figure 5:
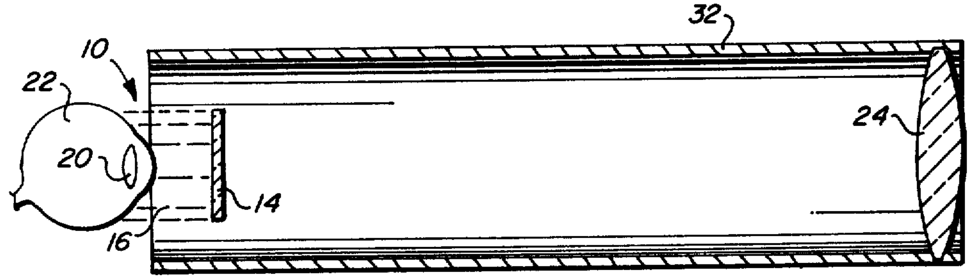
FIG. 5 illustrates another embodiment of the wet cornea telescope of the present invention which includes a hollow tubular member positioned between the eyepiece and the positive lens of the present invention.

FIG. 5 illustrates that lens 24 can be coupled to one end of a hollow tubular member 32 while the second end of tubular member 32 can be positioned around eyepiece 10 as illustrated. Tubular member 32 serves two purposes. First, it substantially decreases light scattering by incorporating opaque side walls which prevent external light transmission into the optical path within the telescope. Second, tubular member 32 can serve as a physical brace or frame for maintaining eyepiece 10 and lens 24 in alignment at a fixed separation distance. If desired, tubular member 32 can be loosely coupled to eyepiece 10 to permit the separation between lens 24 and eyepiece 10 to be varied as desired to properly focus the telescope.

Figure 6:
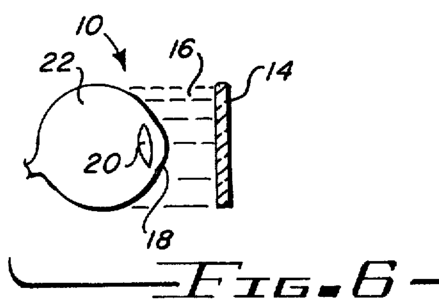
FIG. 6 illustrates an embodiment of the present invention which incorporates an achromatic lens.

FIG. 6 illustrates an additional embodiment of the wet cornea telescope of the present invention in which a positive achromatic lens 34 is incorporated. Achromatic lenses are well known to those skilled in the art and substantially reduce the chromatic abberation which is introduced by most lenses. Utilization of achromatic lens 34 in the present invention substantially increases the clarity of the image observed by the viewer and renders the colors perceived by the viewer virtually totally correct. The presence of the fluid within cavity 16 in contact with cornea 18 also substantially reduces the chromatic aberration so that the telescope system illustrated in FIG. 6 reproduces a substantially magnified image on the viewer's retina with virtually no chromatic aberration of any kind. If desired, non-reflective optical coatings of a type well known to those skilled in the art can be positioned on both the front and rear surfaces on lens 34 and can be added to the front surface of window 14.

Figure 7:
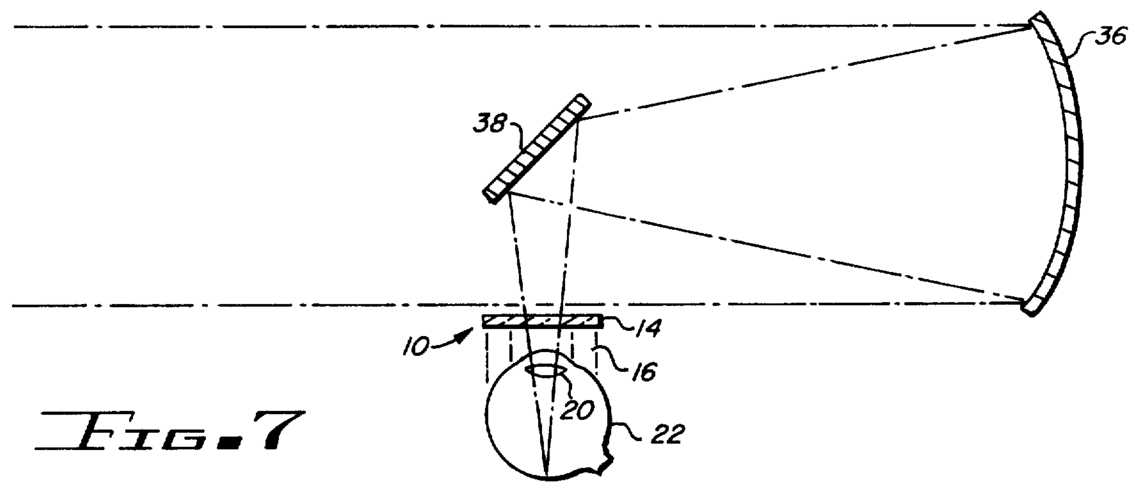
FIG. 7 illustrates another embodiment of the present invention which includes converging means in the form of a parabolic mirror.

Referring now to FIG. 7, a converging means of a different type is illustrated. In this embodiment of the wet cornea telescope a parabolic mirror 36 receives and converges light rays reflected from the object being viewed. A secondary mirror 38 is positioned near the focal plane of mirror 36 and is inclined at an angle to mirror 36 and to window 14 to project light rays through eyepiece 10 in the position illustrated. Mirrors 36 and 38 can be mounted in many ways well known to those skilled in the art. Physically mounting these mirrors to a hollow tubular member of the type illustrated in FIG. 5 would permit the fabrication of a very inexpensive, high power, wet cornea telescope.

Figure 8:
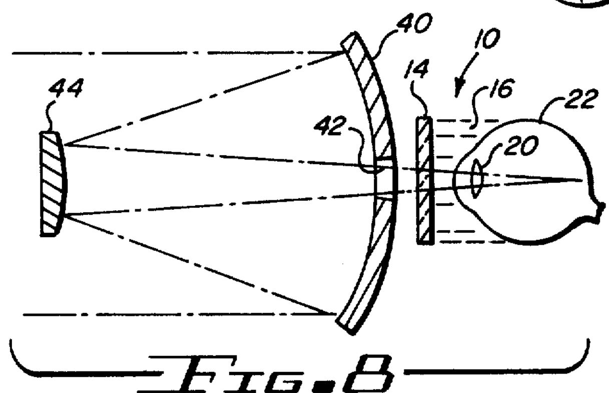
FIG. 8 illustrates still another embodiment of the present invention which includes converging means in the form of a parabolic mirror having an aperture in the center thereof.

FIG. 8 illustrates yet another embodiment of the present invention in which a primary parabolic mirror 40 includes an aperture 42 at its center. A secondary mirror 44 is positioned near the focal plane of mirror 40 in order to reflect converged light rays from mirror 40 through aperture 42 into eyepiece 10 of the present invention.

Figure 9:
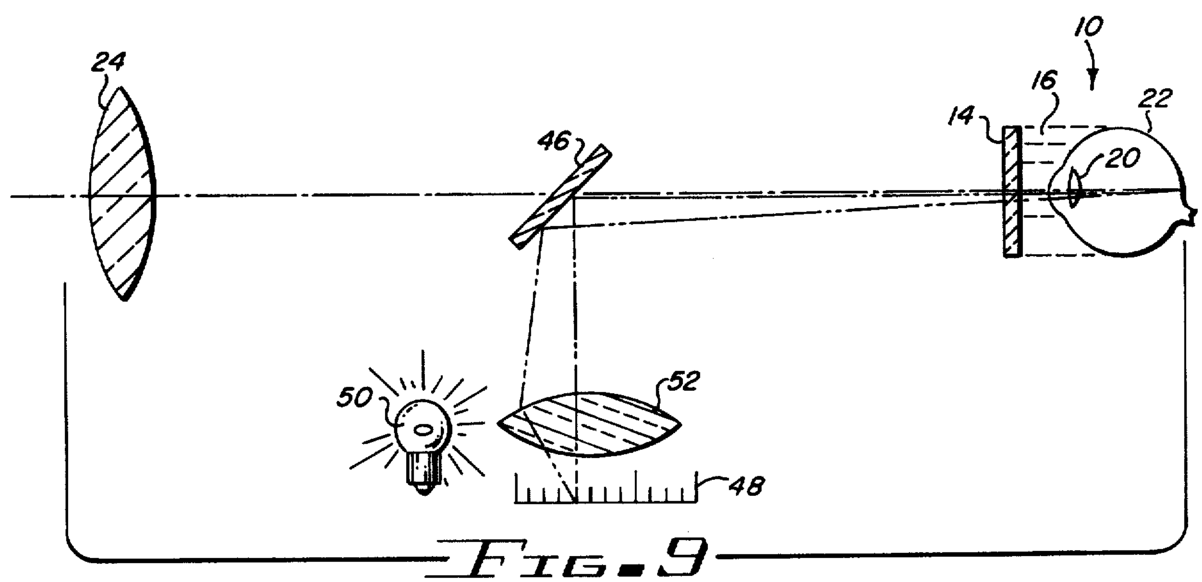
FIG. 9 illustrates that another embodiment of the present invention which includes means for projecting a reticle into the light path between a positive lens and the eyepiece of the present invention.

FIG. 9 illustrates still another variation of the wet cornea telescope of the present invention. In this embodiment an unsilvered glass mirror 46 is positioned in the light path between lens 24 and eyepiece 10 and is inclined at an angle as shown. Mirror 46 permits light waves to be freely transmitted without reflection from lens 24 to eyepiece 10. A reticle scale 48 is illuminated by a light source 50. The light waves generated by light source 50 are reflected from reticle scale 48 and pass through positive lens 52. These light rays are converged by lens 52 and focused on mirror 46 which causes them to be reflected and transmitted through eyepiece 10 of the telescope. In this embodiment the viewer not only sees a highly magnified image of the object being viewed, but also is able to view the superimposed reticle scale 48 in order to compare the unknown dimension of the object being viewed with the graduated reticle scale 48.

Referring now to FIGS. 12, 13 and 14, means is illustrated for filling and draining fluid from cavity 16. FIGS. 12 and 13 illustrate that a valve 54 includes a plug 56 which can be readily displaced from a matted aperture 58 positioned in the upper wall of eyepiece 10. Plug 56 is deflected as illustrated in FIG. 13 by a tube 60. When utilizing this embodiment of the present invention, a user can first secure eyepiece 10 in the desired position on his face and can then introduce tube 60 through aperture 58 and introduce a sufficient amount of fluid to completely immerse cornea 18 of eye 22. Generally, cavity 16 will be completely filled with fluid.

In the more sophisticated wet cornea telescope embodiment illustrated in FIG. 14, eyepiece 10 includes a pair of apertures 62 and 64. A first tube 66 has one end coupled to aperture 66 as shown and another end which is coupled to a collapsible air chamber 68. A clamp 70 permits the air flow between air chamber 68 and fluid chamber 16 to be controlled as desired. A fluid chamber 72 is coupled to aperture 64 by tube 74 as illustrated. Clamp 76 controls the flow of fluid between fluid chamber 72 and fluid chamber 16.

After the viewer has properly positioned eyepiece 10, clamps 70 and 76 will be removed and the walls of fluid chamber 72 will be displaced to cause a flow of fluid from fluid chamber 72 through tube 74 into the interior of fluid chamber 16. The air displaced from fluid chamber 16 will pass through tube 66 into air chamber 68 causing its internal volume to be increased. When fluid chamber 16 has been completely filled, clamps 70 and 76 will be repositioned as illustrated. To drain fluid from fluid chamber 16, clamps 70 and 76 are once again removed and the walls of air chamber 68 are displaced causing fluid to be transferred through tube 74 into the interior of fluid chamber 72. Various types of clamps and various other types of means for draining and filling fluid from chamber 16 will be readily apparent to those skilled in the art.

Since the wet cornea telescope of the present invention can be mass produced very inexpensively and since this device produces a high quality, highly magnified image, it could be readily marketed as either a scientific telescope or as a comparatively indestructible toy. The numerous different wet cornea telescope embodiments discussed above can be further modified by utilizing various different types of lenses. These modifications are too numerous to mention but will be readily apparent to anyone skilled in the art.

It will be apparent to those skilled in the art that the disclosed wet cornea telescope may be modified in numerous other ways and may assume many other embodiments other than the preferred forms specifically set out and described above. For example, transparent window 14 could be formed in the configuration of a negative lens in order to function in a manner similar to the telescope embodiment illustrated in FIG. 4 without the requirement for the additional negative lens 26. In addition, the wet cornea telescope of the present invention can also include a second eyepiece as illustrated in FIG. 1 which would function in combination with a second converging means properly aligned therewith to produce a binocular magnification device while still falling within the scope of the present invention.

I claim:

1. A wet cornea telescope for permitting a viewer to see a magnified image of a remotely positioned object aligned with the optical axis of the telescope, comprising:

a. a liquid-filled eyepiece coupled to the face of the viewer for forming an optically transparent, liquid-filled chamber, said eyepiece including
   i. a flat, substantially non-magnifying, optically transparent window aligned with the optical axis of the telescope and spaced apart from the cornea of said eye;
   ii. a sidewall for maintaining said window spaced apart from said eye, said sidewall having a continuous front end surface for forming a leak-free seal between said eyepiece and said window and a continuous rear end surface for forming a leak-free seal between said eyepiece and the viewer's face; and b. means interposed in the optical path between the object and said eyepiece for converging light rays traveling from the object to the viewer's eye to thereby project a magnified image of the object on the viewer's retina.

2. The telescope of claim 1 further including means coupled to said eyepiece and to the viewer for maintaining the eyepiece in a fixed position on the face of the viewer.

3. The telescope of claim 2 wherein said eyepiece maintaining means includes a strap having a first end coupled to one side of said eyepiece and a second end coupled to the other side of said eyepiece.

4. The telescope of claim 1 wherein the chamber of said eyepiece is filled with water.

5. The telescope of claim 1 wherein the chamber of said eyepiece is filled with a saline solution.

6. The telescope of claim 1 wherein the chamber of said eyepiece is filled with a solution of water and sugar.

7. The telescope of claim 1 wherein the index of refraction of the fluid within the chamber of said eyepiece is approximately the same as the index of refraction of the fluid within the viewer's eye.

8. The telescope of claim 1 wherein said transparent window has a neutral magnification.

9. The telescope of claim 1 wherein said window includes a negative lens for causing the light rays travelling through said window to diverge.

10. The telescope of claim 1 wherein said converging means includes a positive lens.

11. The telescope of claim 10 wherein said positive lens is an achromatic lens.

12. The telescope of claim 10 wherein said lens includes a non-reflective optical coating.

13. The telescope of claim 10 wherein said positive lens has a predetermined focal length and wherein said lens is positioned in front of said window at a distance less than the focal length of said lens.

14. The telescope of claim 10 wherein said positive lens includes a predetermined focal length, said positive lens being separated from said transparent window by distance greater than the focal length of said positive lens, and wherein a second positive lens is positioned in the optical path between said object and said transparent window at a point between the focal length of said positive lens and said transparent window.

15. The telescope of claim 1 further including:

(a) a reticle; and (b) means for projecting said reticle through said transparent window into the viewer's eye without blocking the optical path between the object and said window.

16. The telescope of claim 15 wherein said projecting means includes:

(a) a transparent mirror positioned in the light path between the object and said window and inclined at an angle thereto; and (b) a positive lens positioned between said reticle and said mirror for focusing the light rays transmitted from said reticle to said mirror.

17. The telescope of claim 16 further including means for illuminating said reticle.

18. The telescope of claim 17 wherein said illuminating means includes a light bulb.

19. The telescope of claim 1 further including means for filling said eyepiece with fluid.

20. The telescope of claim 19 wherein said filling means further includes a valve in said eyepiece for permitting fluid to be injected into the chamber of said eyepiece.

21. The telescope of claim 19 wherein said eyepiece further includes means for draining fluid from the chamber.

22. The telescope of claim 1 wherein said converging means includes a parabolic mirror.

23. The telescope of claim 22 further including means positioned in the light path between the object and said parabolic mirror for transmitting the converged light rays from said parabolic mirror through said transparent window when said eyepiece is positioned outside of the light path between the object and said parabolic mirror.

24. The telescope of claim 22 wherein said transmitting means does not interfere with the passage of light rays from the object of said parabolic mirror.

25. The telescope of claim 24 wherein said transmitting means includes a transparent mirror inclined at an angle to the light path between the object and said parabolic mirror.

26. The telescope of claim 22 wherein said parabolic mirror includes a focal point, an aperture in the center of said mirror, and reflecting means positioned at the focal point of said parabolic mirror for reflecting converged light rays from the object through the aperture in said parabolic mirror.

27. The telescope of claim 26 wherein said reflecting means includes a mirror.

28. The telescope of claim 1 further including a tubular member having one end coupled around said converging means and a second end coupled to said eyepiece for maintaining said converging means and said eyepiece in fixed relative positions.

29. The telescope of claim 28 wherein the sidewalls of said tubular member are opaque.

30. The telescope of claim 1 further including a negative lens positioned between said converging means and said transparent window.

31. The telescope of claim 13 further including a negative lens positioned between said converging means and said transparent window.

32. A wet cornea telescope for permitting a viewer to see a magnified image of a remotely positioned object aligned with the optical axis of the telescope, comprising:

a. a liquid-filled eyepiece coupled to the face of the viewer for forming an optically transparent, liquid-filled chamber, said eyepiece including i. a flat, substantially non-magnifying optically transparent window aligned with the optical axis of the telescope and spaced apart from the cornea of the eye;

ii. a sidewall for maintaining said window spaced apart from said eye, said sidewall having a continuous front end surface for forming a leak-free seal between said eyepiece and said window and a continuous rear end surface for forming a leak-free seal between said eyepiece and the viewer's face; and b. a positive lens having a fixed focal length interposed in the optical path between the object and said eyepiece for converging the light rays travelling from the object to the viewer's eye, said positive lens being positioned at a distance less than the focal length of said lens from said transparent window; and c. a hollow tubular member having a first end coupled to said positive lens and a second end positionable about said eyepiece to maintain said positive lens in alignment with said transparent window and to maintain a predetermined distance between said positive lens and said eyepiece.

33. The telescope of claim 32 wherein said tubular member includes opaque sidewalls.

34. The telescope of claim 32 wherein the chamber of said eyepiece is filled with water.

35. The telescope of claim 32 wherein said positive lens includes an achromatic lens.

36. The telescope of claim 32 further including a strap having a first end coupled to one side of said eyepiece and a second end coupled to the other side of said eyepiece and passing around the head of the viewer to maintain said eyepiece in a fixed position on the face of the viewer.

37. The telescope of claim 32 further including a second eyepiece substantially identical to said eyepiece coupled to the face of the viewer and aligned with the viewer's other eye and a second positive lens interposed in the optical path between the object and said second eyepiece.

38. The telescope of claim 37 further including a second hollow tubular member having a first end coupled to said second positive lens and a second end positionable about said second eyepiece to maintain said second positive lens in alignment with said transparent window and to maintain a predetermined fixed distance between said second positive lens and said second eyepiece.

39. The telescope of claim 37 wherein said first and second positive lenses have the same index of refraction.

40. The telescope of claim 39 wherein the spacing between said second positive lens and said second eyepiece is equal to the spacing between said positive lens and said eyepiece.

* * * * *